(12) United States Patent
Schwarz

(10) Patent No.: US 12,220,380 B2
(45) Date of Patent: Feb. 11, 2025

(54) METHODS AND DEVICES FOR TISSUE TREATMENT USING MECHANICAL STIMULATION AND ELECTROMAGNETIC FIELD

(71) Applicant: BTL MEDICAL SOLUTIONS A.S., Prague (CZ)

(72) Inventor: Tomáš Schwarz, Prague (CZ)

(73) Assignee: BTL Medical Solutions A.S., Prague (CZ)

( * ) Notice: Subject to any disclaimer, the term of this patent is extended or adjusted under 35 U.S.C. 154(b) by 0 days.

(21) Appl. No.: 18/051,748

(22) Filed: Nov. 1, 2022

(65) Prior Publication Data

US 2023/0146988 A1 May 11, 2023

Related U.S. Application Data

(63) Continuation of application No. 16/134,116, filed on Sep. 18, 2018, now Pat. No. 11,484,724, which is a continuation-in-part of application No. 15/471,946, filed on Mar. 28, 2017, now Pat. No. 10,080,906, which is a continuation-in-part of application No. 14/870,713, filed on Sep. 30, 2015, now Pat. No. 9,636,516.

(51) Int. Cl.
*A61H 9/00* (2006.01)

(52) U.S. Cl.
CPC ..... *A61H 9/005* (2013.01); *A61H 2201/0214* (2013.01); *A61H 2201/10* (2013.01); *A61H 2230/50* (2013.01)

(58) Field of Classification Search
CPC .... A61H 9/0007; A61H 9/005; A61H 9/0071; A61H 23/008; A61H 23/006; A61H 23/06; A61H 2023/002
See application file for complete search history.

(56) References Cited

U.S. PATENT DOCUMENTS

| | | | | |
|---|---|---|---|---|
| 1,964,590 | A | * | 6/1934 | Muller .................. A61H 9/005 601/67 |
| 3,163,161 | A | * | 12/1964 | Courtin ................ A61H 9/0071 601/16 |
| 4,417,480 | A | | 11/1983 | Zacharias, Jr. |
| 5,143,063 | A | | 9/1992 | Fellner |

(Continued)

FOREIGN PATENT DOCUMENTS

| | | |
|---|---|---|
| AU | 2015202196 | 5/2015 |
| AU | 2016277677 | 1/2017 |

(Continued)

OTHER PUBLICATIONS

Combination 850, model 90 (36 pp, 1999).

(Continued)

*Primary Examiner* — Valerie L Woodward
(74) *Attorney, Agent, or Firm* — Riverside Law LLP

(57) ABSTRACT

Devices and methods for tissue treatment produce a mechanical stimulation therapy and electromagnetic field therapy. The mechanical stimulation therapy provides stimulation of blood circulation and stimulates treated cells. The electromagnetic field enables thermal treatment of tissue. Combination of both therapies improves soft tissue treatment, mainly connective tissue in the skin area and fat reduction.

20 Claims, 7 Drawing Sheets

(56) References Cited

U.S. PATENT DOCUMENTS

| | | |
|---|---|---|
| 5,868,756 A | 2/1999 | Henry |
| 6,036,661 A | 3/2000 | Schwarze |
| 6,104,959 A | 8/2000 | Spertell |
| 6,186,963 B1 | 2/2001 | Schwarze |
| 6,203,521 B1 | 3/2001 | Menne |
| 6,306,152 B1 | 10/2001 | Verdonk |
| 6,334,074 B1 | 12/2001 | Spertell |
| 6,348,338 B1 | 2/2002 | Wittig |
| 6,368,292 B1 | 4/2002 | Ogden |
| 6,375,651 B2 | 4/2002 | Grasso, III |
| 6,390,995 B1 | 5/2002 | Ogden |
| 6,413,230 B1 | 7/2002 | Haupt |
| 6,430,446 B1 | 8/2002 | Knowlton |
| 6,440,105 B1 | 8/2002 | Menne |
| 6,533,792 B2 | 3/2003 | Menne |
| 6,558,397 B2 | 5/2003 | Hirt |
| 6,605,080 B1 | 8/2003 | Altshuler |
| 6,616,618 B2 | 9/2003 | Hagelauer |
| 6,662,054 B2 | 12/2003 | Kreindel |
| 6,673,096 B2 | 1/2004 | Lach |
| 6,702,808 B1 | 3/2004 | Kreindel |
| 6,726,681 B2 | 4/2004 | Grasso, III |
| 6,736,784 B1 | 5/2004 | Menne |
| 6,755,796 B2 | 6/2004 | Spector |
| 6,889,090 B2 | 5/2005 | Kreindel |
| 6,939,344 B2 | 9/2005 | Kreindel |
| 7,011,521 B2 | 3/2006 | Sierro |
| 7,033,382 B2 | 4/2006 | Lach |
| 7,104,983 B2 | 9/2006 | Grasso, III |
| 7,189,209 B1 | 3/2007 | Ogden |
| 7,238,183 B2 | 7/2007 | Kreindel |
| 7,311,678 B2 | 12/2007 | Spector |
| 7,364,554 B2 | 4/2008 | Bolze |
| 7,470,274 B2 | 12/2008 | Lebet |
| 7,470,420 B2 | 12/2008 | Singaram |
| 7,497,834 B2 | 3/2009 | Schaden |
| 7,497,835 B2 | 3/2009 | Schultheiss |
| 7,497,836 B2 | 3/2009 | Schultheiss |
| 7,507,213 B2 | 3/2009 | Schultheiss |
| 7,537,572 B2 | 5/2009 | Schultheiss |
| 7,544,171 B2 | 6/2009 | Schaden |
| 7,578,796 B2 | 8/2009 | Schultheiss |
| 7,594,930 B2 | 9/2009 | Warlick |
| 7,600,343 B2 | 10/2009 | Schultheiss |
| 7,601,127 B2 | 10/2009 | Schultheiss |
| 7,643,883 B2 | 1/2010 | Kreindel |
| 7,695,443 B2 | 4/2010 | Voss |
| 7,775,995 B2 | 8/2010 | Voss |
| 7,785,358 B2 | 8/2010 | Lach |
| 7,841,995 B2 | 11/2010 | Schultheiss |
| 7,857,775 B2 | 12/2010 | Rosenberg |
| 7,867,178 B2 | 1/2011 | Simnacher |
| 7,883,482 B2 | 2/2011 | Schultheiss |
| 7,905,845 B2 | 3/2011 | Schultheiss |
| 7,988,648 B2 | 8/2011 | Warlick |
| 8,034,004 B2 | 10/2011 | Menne |
| 8,057,411 B2 | 11/2011 | Warlick |
| 8,073,550 B1 | 12/2011 | Spertell |
| 8,088,073 B2 | 1/2012 | Simnacher |
| 8,092,401 B2 | 1/2012 | Schultheiss |
| 8,099,154 B1 | 1/2012 | Wess |
| 8,105,254 B2 | 1/2012 | Guantera |
| 8,162,859 B2 | 4/2012 | Schultheiss |
| 8,257,282 B2 | 9/2012 | Uebelacker |
| 8,273,037 B2 | 9/2012 | Kreindel |
| 8,414,472 B2 | 4/2013 | Hagelauer |
| 8,435,194 B2 | 5/2013 | Dverin |
| 8,500,665 B2 | 8/2013 | Schulz |
| 8,506,506 B2 | 8/2013 | Nebrigic |
| 8,514,184 B2 | 8/2013 | Hartl |
| 8,529,451 B2 | 9/2013 | Warlick |
| 8,535,249 B2 | 9/2013 | Uebelacker |
| 8,567,407 B1 | 10/2013 | Kimani Mwangi |
| 8,700,176 B2 | 4/2014 | Azar |
| 8,728,809 B2 | 5/2014 | Cioanta |
| 8,778,414 B2 | 7/2014 | Warlick |
| 8,788,060 B2 | 7/2014 | Nebrigic |
| 8,858,471 B2 | 10/2014 | Barthe |
| 8,961,441 B2 | 2/2015 | Cioanta |
| 9,060,525 B2 | 6/2015 | Warlick |
| 9,123,326 B2 | 9/2015 | Goldenstedt |
| 9,149,322 B2 | 10/2015 | Knowlton |
| 9,452,302 B2 | 9/2016 | Slayton |
| 10,080,906 B2 * | 9/2018 | Schwarz .............. A61N 1/403 |
| 10,166,411 B2 | 1/2019 | Slayton |
| 11,484,724 B2 * | 11/2022 | Schwarz .............. A61B 18/18 |
| 2002/0049483 A1 * | 4/2002 | Knowlton ............. A61B 18/12 |
| | | 607/104 |
| 2003/0176873 A1 | 9/2003 | Chernenko et al. |
| 2004/0073079 A1 * | 4/2004 | Altshuler ............... A61N 7/00 |
| | | 600/1 |
| 2004/0092819 A1 | 5/2004 | Richards |
| 2004/0162582 A1 | 8/2004 | Banziger |
| 2004/0171970 A1 | 9/2004 | Schleuniger |
| 2004/0206365 A1 | 10/2004 | Knowlton |
| 2005/0049543 A1 * | 3/2005 | Anderson ............... A61N 1/40 |
| | | 604/20 |
| 2005/0245791 A1 | 11/2005 | Bauermeister |
| 2006/0025710 A1 | 2/2006 | Schulz |
| 2006/0064864 A1 | 3/2006 | Meissner |
| 2008/0009730 A1 | 1/2008 | Warlick |
| 2008/0009885 A1 | 1/2008 | Del Giglio |
| 2008/0021353 A1 | 1/2008 | Menzi |
| 2008/0033323 A1 | 2/2008 | Meirer |
| 2008/0071198 A1 | 3/2008 | Ogden |
| 2008/0221504 A1 | 9/2008 | Aghion |
| 2008/0228520 A1 | 9/2008 | Day |
| 2008/0312647 A1 * | 12/2008 | Knopp ............... A61B 18/1477 |
| | | 606/41 |
| 2008/0312651 A1 * | 12/2008 | Pope ..................... A61B 18/14 |
| | | 606/42 |
| 2009/0043300 A1 | 2/2009 | Reitmajer |
| 2009/0171266 A1 | 7/2009 | Harris |
| 2009/0171424 A1 | 7/2009 | Britva |
| 2009/0221940 A1 | 9/2009 | Marlinghaus |
| 2009/0248004 A1 | 10/2009 | Altshuler |
| 2009/0326425 A1 * | 12/2009 | Heine .................... A61H 1/008 |
| | | 601/108 |
| 2010/0004568 A1 | 1/2010 | Schwarze |
| 2010/0106064 A1 | 4/2010 | Kreindel |
| 2010/0137752 A1 | 6/2010 | Heine |
| 2010/0137760 A1 | 6/2010 | Schulz |
| 2010/0145241 A1 * | 6/2010 | Heine .................... A61H 23/04 |
| | | 601/107 |
| 2010/0198114 A1 | 8/2010 | Novak |
| 2010/0217165 A1 * | 8/2010 | Muchisky .......... A61H 23/0263 |
| | | 601/93 |
| 2010/0256535 A1 | 10/2010 | Novak |
| 2010/0256536 A1 | 10/2010 | Novak |
| 2010/0286791 A1 | 11/2010 | Goldsmith |
| 2011/0028832 A1 | 2/2011 | Wess |
| 2011/0034832 A1 | 2/2011 | Cioanta |
| 2011/0046523 A1 * | 2/2011 | Altshuler ................ A61N 7/02 |
| | | 601/3 |
| 2011/0245736 A1 | 10/2011 | Foehrenbach |
| 2011/0245740 A1 | 10/2011 | Novak |
| 2011/0275965 A1 | 11/2011 | Donnet |
| 2011/0295160 A1 | 12/2011 | Hart |
| 2011/0306905 A1 | 12/2011 | Novak |
| 2012/0029394 A1 * | 2/2012 | Babaev ................... A61N 7/00 |
| | | 601/2 |
| 2012/0041346 A1 | 2/2012 | Schwarze |
| 2012/0041432 A1 | 2/2012 | Spertell |
| 2012/0150079 A1 * | 6/2012 | Rosenberg ............. A61H 7/008 |
| | | 601/6 |
| 2012/0157892 A1 | 6/2012 | Reitmajer |
| 2012/0191085 A1 | 7/2012 | Eckhouse |
| 2012/0215142 A1 | 8/2012 | Spector |
| 2012/0253240 A1 | 10/2012 | Uebelacker |
| 2012/0265111 A1 | 10/2012 | Glenzer |
| 2012/0271206 A1 | 10/2012 | Shalev |
| 2012/0271289 A1 | 10/2012 | Eckhouse |
| 2012/0310311 A1 | 12/2012 | Elkah |

(56) References Cited

U.S. PATENT DOCUMENTS

| | | |
|---|---|---|
| 2013/0012816 A1 | 1/2013 | Slayton |
| 2013/0018287 A1 | 1/2013 | Capelli |
| 2013/0046207 A1 | 2/2013 | Capelli |
| 2013/0046209 A1 | 2/2013 | Slayton |
| 2013/0066406 A1 | 3/2013 | Spertell |
| 2013/0085551 A1* | 4/2013 | Bachinski .......... A61N 1/36034 607/59 |
| 2013/0123765 A1* | 5/2013 | Zarsky .................. A61N 5/025 607/90 |
| 2013/0144280 A1 | 6/2013 | Eckhouse |
| 2013/0178764 A1* | 7/2013 | Eckhouse ............ A61N 5/0616 601/2 |
| 2013/0303904 A1 | 11/2013 | Barthe |
| 2013/0345600 A1 | 12/2013 | Katragadda |
| 2013/0345684 A1 | 12/2013 | Eckhouse |
| 2014/0088465 A1 | 3/2014 | Cioanta |
| 2014/0104973 A1 | 4/2014 | Donnet |
| 2014/0107542 A1 | 4/2014 | Schubert |
| 2014/0114326 A1 | 4/2014 | Marlinghaus |
| 2014/0128780 A1 | 5/2014 | Kennedy |
| 2014/0135662 A1 | 5/2014 | Britva |
| 2014/0194790 A1 | 7/2014 | Crunick |
| 2014/0222026 A1 | 8/2014 | Tenenbaum |
| 2014/0243715 A1 | 8/2014 | Cioanta |
| 2014/0257144 A1 | 9/2014 | Capelli |
| 2014/0303525 A1* | 10/2014 | Sitharaman ........ A61K 41/0047 601/2 |
| 2014/0330174 A1 | 11/2014 | Warlick |
| 2014/0350438 A1 | 11/2014 | Papirov |
| 2014/0378959 A1 | 12/2014 | Spertell |
| 2015/0005679 A1 | 1/2015 | Becse |
| 2015/0034135 A1 | 2/2015 | Berger |
| 2015/0080771 A1 | 3/2015 | Barthe |
| 2015/0133832 A1* | 5/2015 | Courtion ................ A61H 19/40 601/18 |
| 2015/0141877 A1 | 5/2015 | Feldman |
| 2015/0165238 A1* | 6/2015 | Slayton .................... A61N 7/00 601/2 |
| 2015/0224020 A1 | 8/2015 | Flyash |
| 2015/0224345 A1 | 8/2015 | Warlick |
| 2015/0283026 A1* | 10/2015 | Rosenberg ............ A61H 9/0057 601/10 |
| 2015/0374577 A1 | 12/2015 | Aghion |
| 2016/0000645 A1 | 1/2016 | Cioanta |
| 2016/0008016 A1 | 1/2016 | Cioanta |
| 2016/0016013 A1* | 1/2016 | Capelli ................ A61B 17/225 601/2 |
| 2016/0022294 A1 | 1/2016 | Cioanta |
| 2016/0067139 A1 | 3/2016 | Katragadda |
| 2016/0082290 A1 | 3/2016 | Hart |
| 2016/0089296 A1 | 3/2016 | Swart |
| 2016/0089297 A1 | 3/2016 | Swart |
| 2016/0121112 A1 | 5/2016 | Azar |
| 2016/0228322 A1 | 8/2016 | Rosenberg |
| 2016/0310766 A1 | 10/2016 | Cioanta |
| 2017/0151125 A1 | 6/2017 | Becse |
| 2017/0189867 A1 | 7/2017 | Donnet |
| 2017/0258674 A1 | 9/2017 | Morganstern |
| 2017/0296427 A1 | 10/2017 | Warlick |
| 2017/0360654 A1 | 12/2017 | Papirov |
| 2018/0008297 A1 | 1/2018 | Ein-Gal |
| 2018/0049943 A1 | 2/2018 | Warlick |
| 2018/0116905 A1 | 5/2018 | Capelli |
| 2018/0137260 A1 | 5/2018 | McGhin |
| 2018/0147111 A1 | 5/2018 | Gaines |
| 2018/0193046 A1 | 7/2018 | Griffis |
| 2018/0221688 A1 | 8/2018 | Cioanta |
| 2018/0228638 A1 | 8/2018 | Spector |
| 2018/0296432 A1 | 10/2018 | Warlick |
| 2018/0325959 A1 | 11/2018 | Ichim |
| 2018/0333565 A1 | 11/2018 | Ein-Gal |
| 2018/0369061 A1 | 12/2018 | Aghion |
| 2019/0142692 A1 | 5/2019 | Becse |
| 2019/0143148 A1 | 5/2019 | Slayton |
| 2019/0167511 A1 | 6/2019 | Morganstern |
| 2019/0192377 A1 | 6/2019 | Kaila |
| 2019/0209427 A1 | 7/2019 | Warlick |
| 2019/0209431 A1 | 7/2019 | Warlick |
| 2019/0231639 A1 | 8/2019 | Papirov |
| 2020/0038138 A1 | 2/2020 | Lebreton |
| 2020/0043682 A1 | 2/2020 | Lebreton |
| 2020/0113777 A1 | 4/2020 | Novak |

FOREIGN PATENT DOCUMENTS

| | | |
|---|---|---|
| AU | 2017232035 | 4/2019 |
| AU | 2017232036 | 4/2019 |
| CN | 202113500 | 1/2012 |
| CN | 202459228 | 10/2012 |
| CN | 103040608 | 4/2013 |
| CN | 203507323 | 4/2014 |
| CN | 203915068 | 11/2014 |
| CN | 104998354 | 10/2015 |
| CN | 205007456 | 2/2016 |
| CN | 105769260 | 7/2016 |
| CN | 105997468 | 10/2016 |
| CN | 106310530 | 1/2017 |
| CN | 205885974 | 1/2017 |
| CN | 206880834 | 1/2018 |
| CN | 207012336 | 2/2018 |
| CN | 207821872 | 9/2018 |
| DE | 102007013288 | 9/2008 |
| DE | 102007030670 | 1/2009 |
| DE | 102009004971 | 4/2010 |
| DE | 202010009899 | 10/2010 |
| DE | 202009011534 | 12/2010 |
| DE | 202010015258 | 2/2012 |
| DE | 102012220121 | 9/2013 |
| DE | 202013010118 | 4/2014 |
| DE | 202015008586 | 1/2016 |
| DE | 202016001365 | 4/2016 |
| DE | 202015005070 | 10/2016 |
| DE | 102016219115 | 4/2018 |
| EP | 1154727 | 11/2001 |
| EP | 1502626 | 2/2005 |
| EP | 2351530 | 8/2011 |
| EP | 2529678 | 12/2012 |
| EP | 2529679 | 12/2012 |
| EP | 3000420 | 3/2016 |
| EP | 3047809 | 7/2016 |
| EP | 3124004 | 2/2017 |
| EP | 3235454 | 10/2017 |
| JP | 2011194176 | 10/2011 |
| KR | 100698582 | 3/2007 |
| KR | 100783507 | 12/2007 |
| KR | 100864310 | 10/2008 |
| KR | 20100004810 | 1/2010 |
| KR | 100991846 | 11/2010 |
| KR | 101234682 | 2/2013 |
| KR | 20130054874 | 5/2013 |
| KR | 200469045 | 9/2013 |
| KR | 20190028411 | 3/2019 |
| KR | 101967355 | 4/2019 |
| KR | 20190042923 | 4/2019 |
| WO | 9710758 | 3/1997 |
| WO | 2017165595 | 9/2017 |
| WO | 2018002929 | 1/2018 |
| WO | 2018017414 | 1/2018 |
| WO | 2018136514 | 7/2018 |
| WO | 2019123027 | 6/2019 |
| WO | 2019132227 | 7/2019 |
| WO | 2019146883 | 8/2019 |

OTHER PUBLICATIONS

Cynosure Cellulaze (8 pp, 2012).
Gerdesmeyer, L., et al., Radial Extracorporeal Shockwave Therapy (rESWT) in Orthapaedics. J. Minerals. (4 pages) Munich, Germany. 11(4): 36-39; 2004.
Lipolys AMI RSWT Lipokontur (2 pp).
Office Action (Notice of Allowance and Fees Due (PTOL-85)) dated Jun. 27, 2022 for U.S. Appl. No. 16/134,116 (pp. 1-5).

(56) References Cited

OTHER PUBLICATIONS

Office Action dated Jul. 22, 2021 for US App. No. 16/134,116 (pp. 1-15).
Schlaudraff KU, Kiessling MC, Császár NB, Schmitz C. Predictability of the individual clinical outcome of extracorporeal shock wave therapy for cellulite. Clin Cosmet Investig Dermatol. May 23, 2014;7:171-83.
Storz Medical, Cellactor SC1 Application Brochure (24 pp).
VelaShape III (7 pp, 2014).

\* cited by examiner

METHODS AND DEVICES FOR TISSUE TREATMENT USING MECHANICAL STIMULATION AND ELECTROMAGNETIC FIELD

PRIORITY CLAIM

This Application is a continuation of U.S. patent application Ser. No. 16/134,116, filed on Sep. 18, 2018, now pending, which is a continuation-in-part of U.S. patent application Ser. No. 15/471,946, filed on Mar. 28, 2017, now U.S. Pat. No. 10,080,906, which is a continuation-in-part of U.S. patent application Ser. No. 14/870,713 filed Sep. 30, 2015, now U.S. Pat. No. 9,636,516, all of which are incorporated herein by reference in their entireties.

FIELD OF THE INVENTION

The invention relates to method and device for soft tissue treatment, mainly connective tissue in the skin area and fat reduction.

BACKGROUND OF THE INVENTION

Human skin is tissue which is commonly treated in order to improve its visual appearance. Skin is composed of three basic elements: the epidermis, the dermis and the hypodermis or so called subcutis. The outer and also thinnest layer of skin is the epidermis. Epidermis contains mainly stratified squamous epithelium of which the outer side keratinizes and ensures coverage whereas the inner side contains a pigment. The dermis consists of collagen, elastic tissue and reticular fibers. The hypodermis is the lowest layer of the skin and contains hair follicle roots, lymphatic vessels, collagen tissue, nerves and also fat forming a subcutaneous white adipose tissue (SWAT).

SWAT is formed by aggregation of fat cells ranging up to 120 microns in diameter and containing as much as 95% glycerides and fatty acids by volume. Overeating and unhealthy lifestyles may result in an increase of size and/or number of the fat cells. The fat cells create lobules which are bounded by connective tissue, fibrous septa (retinaculum cutis).

Another part of adipose tissue is located in peritoneal cavity and is known as abdominal obesity. Visceral fat layer forming visceral white adipose tissue (VWAT) is located between parietal peritoneum and visceral peritoneum, closely below muscle fibers adjoining the hypodermis layer.

Excess of adipose tissue in subcutaneous or abdominal area may be perceived as aesthetically undesirable, mainly in the buttocks, thighs, abdomen or hips, where even weight loss after dieting and exercise may not lead to satisfactory results. Moreover, in the last few decades, more people suffer from growth of visceral white adipose tissue (VWAT) mainly in their abdominal area. Visceral fat has been also linked to various cardiovascular diseases and diabetes.

The undesirable topographic skin appearance may also be caused by changes in dermal or sub-dermal layer of the skin, especially by excessive number or volume of fat cells, weakening of fibrous septas, loss of elasticity and/or limited lymph flow, which may result in accumulation of toxins.

Mechanical stimulation includes acoustic, ultrasound and/or shock waves. Shock waves are waves characterized by steep pressure amplitude growth in comparison to the surrounding pressure. Despite their relationship with other types of mechanical stimulation, shock waves are different mainly in pressure magnitude and shape of the pressure wave. In comparison to ultrasound waves where the pressure periodically oscillates with limited bandwidth and amplitude, shock waves are characterized by non-linearity during the wave propagation. In the present invention, shock wave propagation is characterized by swift positive pressure increase in the range from one nanosecond up to 100 microseconds with positive peak pressure amplitudes up to 150 MPa. In comparison, regular ultrasound methods have positive peak pressure amplitudes up to about 3 MPa. The pulse duration (based on the time the pressure exceeds a half value of peak positive pressure) is preferably in the range of hundreds of nanoseconds to 10-100 of microseconds.

There are four main principles for generating shock waves: electrohydraulic, piezoelectric, electromagnetic and ballistic. The shock waves produced by electrohydraulic principle, piezoelectric principle or electromagnetic principle are traditionally used for destruction of calculi e.g. kidney stones. As these shock waves are focused, they may be characterized as hard shock waves because the energy is directed into small point in the tissue.

The ballistic shock waves have a naturally non-focused/radial propagation. Radial/non-focused propagation is characterized by smooth propagation.

Various non-invasive methods for skin treatment containing light, radiofrequency, microwave, and ultrasound treatment has been previously developed. Nevertheless, improved treatments in aesthetic medicine are needed.

SUMMARY OF THE INVENTION

Methods and devices for a non-invasive treatment of soft tissue including SWAT, VWAT and connective tissue use a mechanical stimulation and electromagnetic field therapy. Methods and devices provide a non-invasive treatment of soft tissue by an electromagnetic field and a mechanical stimulation, which may be an acoustic, ultrasound or shock wave. Methods and devices provide a massage of tissue. The mechanical stimulation may be generated by electrohydraulic, piezoelectric and/or electromagnetic techniques, or pneumatically (including ballistic principle).

A ballistic mechanism of shock wave generation may be used. The ballistic shock wave mechanism contains a projectile striking against an applicator head for generating the shock wave. The ballistic shock wave have a naturally non-focused, planar or moderately focused propagation. Ballistic shock wave methods of propagation are characterized by smooth propagation. Also other non-focused, radial or moderately focused methods may be used. However, methods and devices may also use focused ballistic shock waves, wherein the shock wave may be focused by the shape of a percussion guide.

The electromagnetic field may be generated by energy delivery elements (e.g. LED, lamps, and a bipolar, monopolar, unipolar, multipolar electrodes) in direct, indirect or even noncontact arrangement with the skin surface. The electromagnetic field frequency may be in the range from 0.1 MHz to 10 GHz.

The electromagnetic field may be generated by a laser diode module or a LED. The electromagnetic field wavelength may be preferably in the range from 600 nm to 1200 nm.

Combinations of both therapies provide new soft tissue treatment with reduced risk of adverse effects. Treatment may lead to remodeling of a soft tissue in the skin area including white adipose tissue. Remodeling may include reduction in number and/or volume of the visceral white adipose tissue and/or the subcutaneous white adipose tissue.

Treatment may also lead to improvement of connective tissue elasticity, mainly elasticity of fibrous septae connecting the dermis to underlying fascia.

Although neocollagenesis is normally induced at temperatures higher than 48° C., the combination of mechanical stimulation and an electromagnetic field enables improved results at lower temperatures and with less stress of the tissue. Temperature of the soft tissue during the treatment may be about 32-48° C.

According to another embodiment the temperatures may reach above 50° C. which leads to thermal denaturation of collagen and collagen shrinkage. Temperature of the tissue may also be increased in the range of 37° C. to 200° C.; or 40° C. to 150° C.; or 42° C. to 120° C.; or 43° C. to 95° C.

The sum of the energy flux density of the mechanical stimulation and the electromagnetic field applied to the patient simultaneously, successively or in overlap is typically above 1 mW·mm-2. With the simultaneous method, the electromagnetic field and mechanical stimulation are both used simultaneously during the time interval e.g., 1-10 seconds. In the successive method, an electromagnetic field is used during a first time interval of e.g., 1-5 seconds. The electromagnetic field is then stopped and mechanical stimulation is used in a subsequent time interval of e.g., 6-10 (immediately afterwards the electromagnetic field ends, with the combined application time in this example totaling to 10 seconds). In the overlapping method, an electromagnetic field is used during a first time interval from e.g., 1-7 seconds, and mechanical stimulation is used in a second overlapping time interval of e.g., 4-10 seconds (wherein during the second time interval the electromagnetic field and mechanical stimulation are simultaneously applied over the second interval starting at 4 seconds and ending at 7 seconds).

In comparison with known techniques, the present device and method enable gentle treatment with no surgery and reduced amounts of energy delivered into the tissue.

The present methods and device may provide improved soft tissue treatment, mainly in skin region such improving skin laxity, skin tightening, wrinkles reduction and including fat cells elimination.

GLOSSARY

"Lipolysis" includes apoptosis and/or necrosis of the targeted adipocytes.

"Shockwave" is characterized by swift positive pressure increase in the range from ones of nanoseconds up to tens of microseconds with positive peak pressure amplitudes up to 150 MPa. The pulse duration (based on the time the pressure exceeds a peak positive pressure/2) is approximately in the range of hundreds of nanoseconds to tens of microseconds.

"Soft tissue remodeling" or "remodeling of soft tissues" means reorganization or renovation of existing tissue with improvement of its elasticity and visual appearance, including reduction of white adipose tissue in number and/or volume.

"Massage" means the change of pressure applied onto the tissue related to ambient pressure.

DETAILED DESCRIPTION

Figure 1:
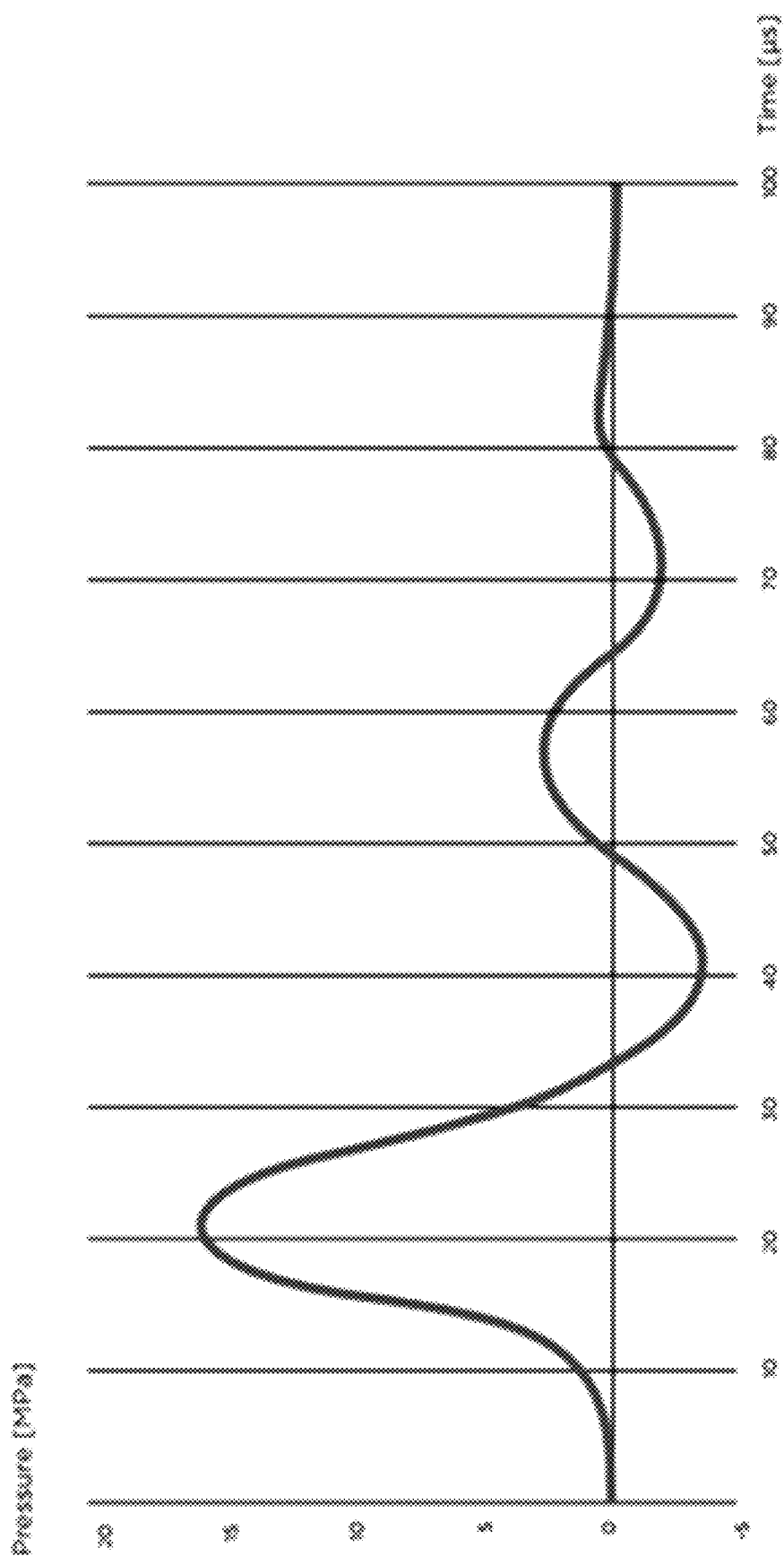
FIG. 1 is an example of mechanical stimulation propagation

FIG. 1 shows an example of mechanical stimulation propagation. Mechanical stimulation e.g. shock waves are characterized by steep pressure amplitude growth in comparison to the surrounding pressure. The mechanical stimulation is characterized by non-linearity during the propagation. The positive peak pressure is above 0.1 MPa, more preferably 3 MPa, even more preferably at least 7 MPa, most preferably at least 15 MPa. The peak pressure in the positive maximum may be up to 150 MPa. The pulse duration of the mechanical stimulation (based on the time the pressure exceeds a half value of peak positive pressure) may be preferably in the range of hundreds of nanoseconds to tens of microseconds.

In comparing mechanical stimulation e.g. ultrasound and shock waves, not only are there differences in the shape and the propagation, but there are also significant differences between the physical effect of ultrasound and shock waves on the treated tissue, and particularly a cavitation effect. Cavitation is formation of gas bubbles in a fluid environment which occurs during the negative pressure wave in the liquid. Ultrasonic cavitation bubbles represent acoustic inhomogeneity in which incoming acoustic energy is absorbed and dissipated. Due to the high frequency of ultrasound waves, the acoustic energy may lead to rapid growth of cavitation bubbles and later to inertial cavitation effects, with breakup of the bubbles and violent damage of the surrounding tissue. Shock waves can reduce cavitation and the violent break up of cells resulting from cavitation.

The repetition rate (frequency) of the mechanical stimulation may be in the range from 0.1 Hz to 100 Hz, more preferably in the range from 0.5 to 50 Hz, most preferably in the range from 1 Hz to 40 Hz.

Four main principles for generating shock waves are described: electrohydraulic, piezoelectric, electromagnetic and pneumatic including ballistic. The shock waves produced by spark discharge, piezoelectric principle or electromagnetic principle are traditionally used for destruction of calculi e.g. kidney stones and based on its propagation it is possible to summarize them as focused. Electrohydraulic, piezoelectric and electromagnetic methods are also sometimes referred as hard shock waves because the energy is directed into small point in the tissue. On the other hand the electrohydraulic, piezoelectric, electromagnetic principle may be suitable if they are non-focused/radial, planar or moderately focused, and therefore softened.

Shock waves have a naturally non-focused/radial, planar or moderately focused propagation. Non-focused/radial, planar shock waves are characterized by smooth/soft propagation and therefore are preferred. The pneumatic principle of generating mechanical stimulation may be performed by pressurized gas vibrating a percussion guide or by ballistic shock waves which may be generated by striking of a bullet inside a guiding tube to a percussion guide. The bullet may be accelerated by pressurized gas, electric field, magnetic field, spring or other technique.

Also other principles (e.g. electrohydraulic, piezoelectric and electromagnetic) for generating non-focused, radial or moderately focused mechanical stimulation may be used. Moderate focus means varying levels of focused ultrasound energy or focal point in a distance longer than the treated tissue extends, where the energy in the focal point is not sufficient to cause harm of tissue.

Mechanical stimulation may be focused by reflectors, piezoelectric sources (mainly by their position and/or shape), or by using one or more focusing lenses. Focusing of the mechanical stimulation may also be provided by the shape of a percussion guide.

In order to achieve the best results in the soft tissue, the energy flux density of the mechanical stimulation is preferably in the range between 0.001 mW·mm-2 and 160 mW·mm-2, more preferably in the range between 0.001 mW·mm-2 and 100 mW·mm-2, most preferably in the range between 0.001 mW·mm-2 and 50 mW·mm-2.

Electromagnetic field used for heating the soft tissue may be radiofrequency field or microwave field, typically in the range of 0.1 MHz to 25 GHz, more preferably in the range from 0.1 MHz to 435 MHz, most preferably in the range from 0.1 MHz to 28 MHz. All the above mentioned waves may cause movement of charged particles e.g. ions, rotation of dipolar molecules or polarization of normally non polar particles and therefore increase the tissue temperature.

The device for proposed therapy may include a bipolar electrode system, where electrodes alternate between active and return function and where the thermal gradient beneath electrodes is almost the same during treatment. Bipolar electrodes may form circular or ellipsoidal shapes, where electrodes are concentric to each other. However, a group of bipolar electrodes may be used as well. Alternatively, a monopolar electrode system may be used. With the monopolar arrangement, the return electrode has a sufficiently large area in comparison to active electrode. The return electrode is in contact with skin of the patient and may by positioned relatively farther from the active electrode. A unipolar electrode may also optionally be used. Both capacitive and resistive electrodes may be used. Optionally one or more inductive electrodes may be used.

One or more multipolar electrodes may be used.

Figure 5A:
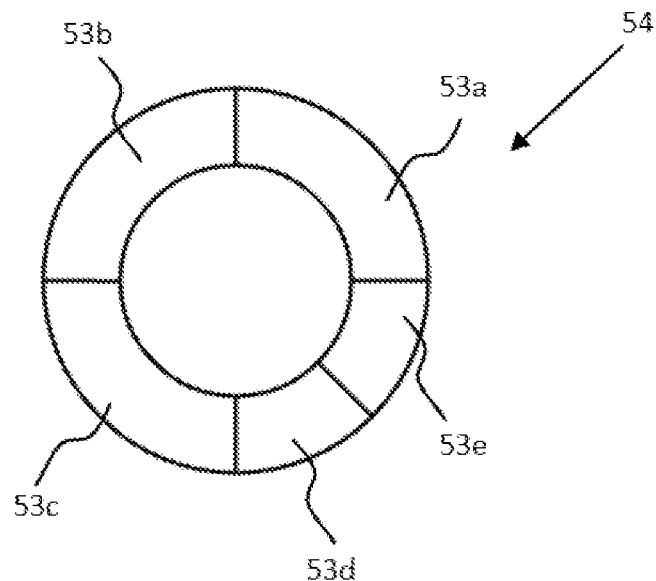
FIG. 5A is a schematic view of a multipolar electrode
Figure 5B:
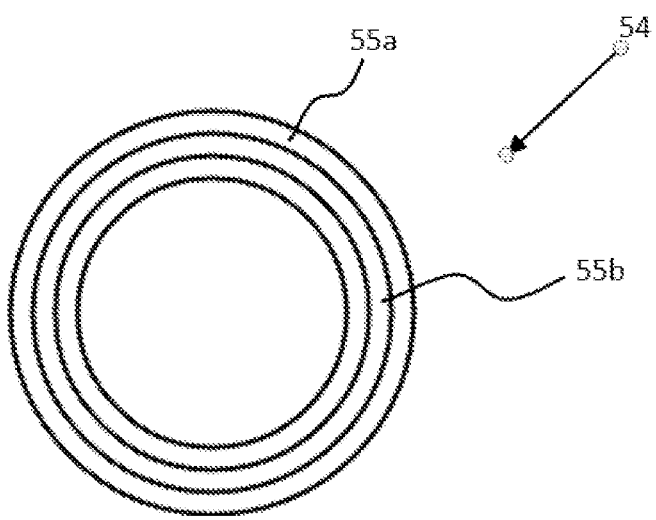
FIG. 5B is a schematic view of another multipolar electrode.

An energy delivery element may be divided into segments to provide treatment of selected parts of the tissue with higher efficiency or in a repeating manner. FIG. 5A shows energy delivery element divided to two or more segments 53*a-d* having the shape of an arc. A negative or positive charge of each segment may alternate. Each segment may be operated independently of other segments. Angular sections of the arc may be in the range of 1° to 359° or 5° to 275° to 15° to 185° or 20° to 95°. FIG. 5B shows energy delivery 54 divided to two or more segments 55*a-d* having the shape of layer, which may be concentric to each other.

In order to increase deep tissue heating by the electromagnetic field, the distance between electrodes may be varied; the electromagnetic field may be phase shifted or modulated; or an external magnetic field may be applied.

The electromagnetic field may be represented by light generated by one or more light sources. The light source may include a light emitting diode, a laser emitting diode, an optical fiber, a flash lamp, a tungsten lamp, an incandescent lamp, a mercury arc or any other light or energy source known in the art. The light may be coherent, incoherent, depolarized and/or polarized light. Coherent monochromatic light may include any type of laser, e.g. a chemical laser, a dye laser, a free-electron laser, a gas dynamic laser, a gas laser (for example an argon laser or carbon dioxide laser), an ion laser, a metal-vapor laser (for example a gold vapor laser and/or a copper vapor laser), a quantum well laser, a diode laser (for example GaAs, AlGaSbAs, InGaAsP/InPm InGaAs) and/or a solid state laser (for example a ruby laser, a Nd:YAG laser, a NdCr:YAG laser, an Er:YAG laser, an Er:glass laser, a Nd:YLF laser, a Nd:YVQ4 laser, a Nd:Y-COB laser, a Nd:Glass laser, a Ti:sapphire laser, a Tm:YAG laser, a Ho:YAG laser or an Er,Cr:YSGG laser). The wavelength of the light may be approximately in the range of 190 nm to 13000 nm or 350 nm to 2500 nm or 400 nm to 2000 nm. Applied light may be monochromatic or polychromatic. Light may be applied in pulses with pulse duration in the range of 0.1 µs to 10000 ms, more preferably in the range of 1 µs to 5000 ms, even more preferably in the range of 2 µs to 2500 ms, most preferably in the range of 5 µs to 1000 ms. Light may be applied close to specific spectral band. Term "close to" refers to deviation of 20%, more preferably 15%, most preferably 10% from the nominal wavelength. Applied spectral bands may be close to 405 nm, 450 nm, 530 nm, 560 nm, 575 nm, 640 nm, 685 nm, 830 nm, 915 nm, 1064 nm, 1280 nm, 1440 nm, 1540 nm, 1550 nm, 1715 nm and/or 2940 nm. Energy flux provided by light may be in the range of 0.005 W·cm-2 to 500 W·cm-2, more preferably in the range of 0.01 W·cm-2 to 150 W·cm-2 and most preferably in the range of 0.01 W·cm-2 to 120 W·cm-2. Spot size, which is defined as surface of tissue treated by the light, may be in the range of 0.01 cm2 to 2000 cm2, more preferably in the range of 0.05 cm2 to 1500 cm2, most preferably in the range of 0.1 cm2 to 850 cm2. The emission output power of the light source may be in the range from about 1 mW to about 150 W. Temperature of the tissue may be increased by the light combined with shockwave energy in the range of 37° C. to 200° C.; or 40° C. to 150° C.; or 42° C. to 120° C.; or 43° C. to 95° C. Together and/or apart of heating, the light may also provide apoptosis, necrosis, coagulation and/or ablation of the tissue. The light (e.g. laser) may provide fractional damage to the epidermis, dermis and/or hypoderm is, wherein fractional damage may include ablation or necrosis. Use of shock wave energy sequential and/or parallel to the light providing fractional damage may also provide treatment benefit by relieving of pain.

The application of shockwave energy and electromagnetic therapy may be combined with application of plasma, e.g. high-thermal plasma, non-thermal plasma, cold plasma and/or ultracold plasma. Types of plasma and types of its generation are described in U.S. patent application Ser. No. 15/786,303, which is incorporated herein by reference.

According to another embodiment, the electromagnetic field may be represented by near infrared waves generated by at least one laser diode module or LED approximately in the range from 600 nm to 1200 nm, more preferably from 630 nm to 990 nm. The emission output power of the laser diode module or LED are in the range from about 10 mW to about 10 W.

Energy flux density of the electromagnetic field is preferably in the range between 0.01 mW·mm$^{-2}$ and 10 000 mW·mm$^{-2}$, more preferably in the range between 0.1 mW·mm$^{-2}$ and 5 000 mW·mm$^{-2}$, most preferably in the range between 0.5 mW·mm$^{-2}$ and 1 000 mW·mm$^{-2}$.

The sum of energy flux density of the mechanical stimulation and electromagnetic field applied to the patient simultaneously, successively or in overlap should be preferably above 0.1 mW·mm$^{-2}$, 1 mW·mm$^{-2}$, or 5 mW·mm$^{-2}$, generally up to a maximum of 100, 500, 1000, 5,000, 10,000 or 15,000 mW·mm$^{-2}$.

Cooling may be provided to the treated and/or untreated tissue. Cooling may be provided by any known mechanism including water cooling, sprayed coolant, presence of the active solid cooling element (e,g, thermocouple) and also by air flow. In one embodiment the device may include an applicator providing cooling together with shock wave energy, wherein methods may include cooling of tissue (e.g. adipose tissue and/or collagen) applied sequentially or in parallel to application of shock wave energy. Also, the methods of treatment may include use of applicator providing cooling and a different applicator providing shock wave energy. Cooling of the tissue may lead to crystallization of highly saturated fatty acids in treated tissue, wherein the crystals may damage cell membranes and induce necrosis and/or apoptosis. Application of shock waves before and/or during the cooling of the tissue may decrease pain and/or uncomfortable perception of the cooling therapy and may lead to movement of the forming and/or already formed fatty acid crystals in the treated tissue (particularly adipose tissue) and therefore to higher damage to cell membranes. Application of shock wave therapy after the cooling of the tissue may improve the blood flow and therefore lead to faster increase of the temperature in the treated tissue and/or body part and may lead to movement of formed fatty acid crystals in the treated tissue and therefore to higher damage to cell membrane.

The device may include a cooling element. The cooling element may include a coolant reservoir, an active solid cooling element and/or a cooled element. The coolant reservoir may include coolant, which may be sprayed onto and/or into tissue and/or used to cooling the cooled element. Coolant may include saline, glycerol, water, alcohol, water/alcohol mixture, cold air and/or liquid nitrogen. The temperature of the coolant may be in the range of $-200°$ C. to $37°$ C. The cooled element may include a thermal conductive material e.g. glass, gel, ice slurry and/or metal. An active solid cooling element may include an Peltier element including active side cooling the tissue and passive side which may be cooled by liquid (e.g. water), gas coolant (e.g. air), coolant and/or another Peltier element. The temperature of the cooling element during the active treatment may be in the range of $-80°$ C. to $37°$ C.; or $-70°$ C. to $37°$ C.; or $-60°$ C. to $35°$ C.

The temperature of the tissue may be decreased to under $37°$ C. The temperature of the tissue may be decreased in the range of $-30°$ C. to $35°$ C. The tissue may be cooled for a time interval of at least 1, 5, 30 or 60 minutes.

In one embodiment, the temperature of treated adipose tissue during one cooling cycle may be in the range of $-10°$ C. to $37°$ C.; or $-5°$ C. to $20°$ C.; or $-3°$ C. to $15°$ C. while the temperature of dermis and/or epidermis is maintained in the temperature range of $-5°$ C. to $15°$ or around the temperature of about $0°$ C. In another embodiment, the temperature of treated collagen tissue during one cooling cycle may be in the range of $-80°$ C. to $37°$ C. or $-75°$ C. to $20°$ C. or $-70°$ C. to $15°$ C. while the temperature of dermis and/or epidermis is maintained in the temperature range of $-5°$ C. to $15°$ or around the temperature of about $0°$ C. The cooling cycle may include application of shock wave energy and/or shock wave energy may be applied during the cooling cycles. The cooling cycle may be in the range of 1 s to 2 hours or 10 s to 40 minutes or 5 minutes to 30 minutes, Treatment may include one or plurality of cooling cycles.

Methods of treatment may further include an application of at least one substance during the application of the energy, wherein the substance may affect the tissue. The substance may be applied before, during and/or after the application of the combination of shock wave energy with electromagnetic energy and/or cooling. The may be applied as aerosol contacting the body, orally, and/or intradermally. The substance may improve treatment results, make treatment more comfortable by e.g. minimizing pain during the treatment and/or safer. The released substances may include oleoresin capsicum (pelegrinacid-vanillilamid) increasing the skin blood flow. Other substances may include lipolysis augmentation agents like: methyl xanthines such as theophylline, aminophylline, caffeine; pentoxifylline; beta-1 adrenergic agonists (stimulators) including, but not limited to: forskolin, norepinephrine, epinephrine, isoproteranol; specific beta-3 agonists (stimulators) including but limited to: fenoterol, clenbuterol; alpha-2 adrenergic inhibitors (antagonists) including but not limited to: yohimbine, rauwolscine, oxymetazoline, piperoxane, phentolamine, dihydroergotamine, idazoxin; adenosine inhibitors; calmodulin agonists; thyroid hormones including but not limited to: T3/triiodothyronine and T4/tetraiodothyronine; sex hormones including but not limited to methyltestosterone; prostaglandin inhibitors including but not limited to aspirin (ASA), non-steroidal anti-inflammatory drugs (NSAID's), and finasteride, tamoxifen, catecholamine, flavanols and the like. The named substances are not a complete list of possible substances, and other substances may be used to provide some or all of the effects described above.

Substances may include alkaloids (e.g. xanthines), antithyroid agents, metformin and/or octreotide modulating normal metabolism and/or basal metabolism rate of the patient's body by acceleration of the metabolism related to the apoptosis. Substances may include prostaglandins and their analogues, modified lipids (e.g. lysophosphatidylserine, lipoxins, resolvins, protectins and/or maresins), lipoprotein lipase inhibitors, nitric oxide secretion stimulators, alkaloids (e.g. xanthines), antioxidants (e.g. ascorbic acid), or derivatives of carbohydrates providing improvement of removal of dying cells.

Substances may include terpens (e.g. forskolin), catecholamins, hormons (e.g. leptin, growth hormone and/or testosterone), alkaloids (e.g. synephrin), phosphodiesterase inhibitors (e.g. xanthins), polyphenols, peptides (e.g. natriuretic peptides), amino acids providing improvement of the lipolysis rate. Substances may also include anesthetics e.g. lidocaine, benzocaine, menthol providing reversible decrease or absence of sensation in the specific part of the patient's body.

The treatment device may include a transmatch adjusting impedance to the impedance of the treated tissue in order to maximize the power transmission. The transmatch may adjust the impedance in order to minimize the reflected power. The device may also include a balun transformer, which may be part of the transmatch. The balun may allow for treatment without need of grounding.

Figure 2:
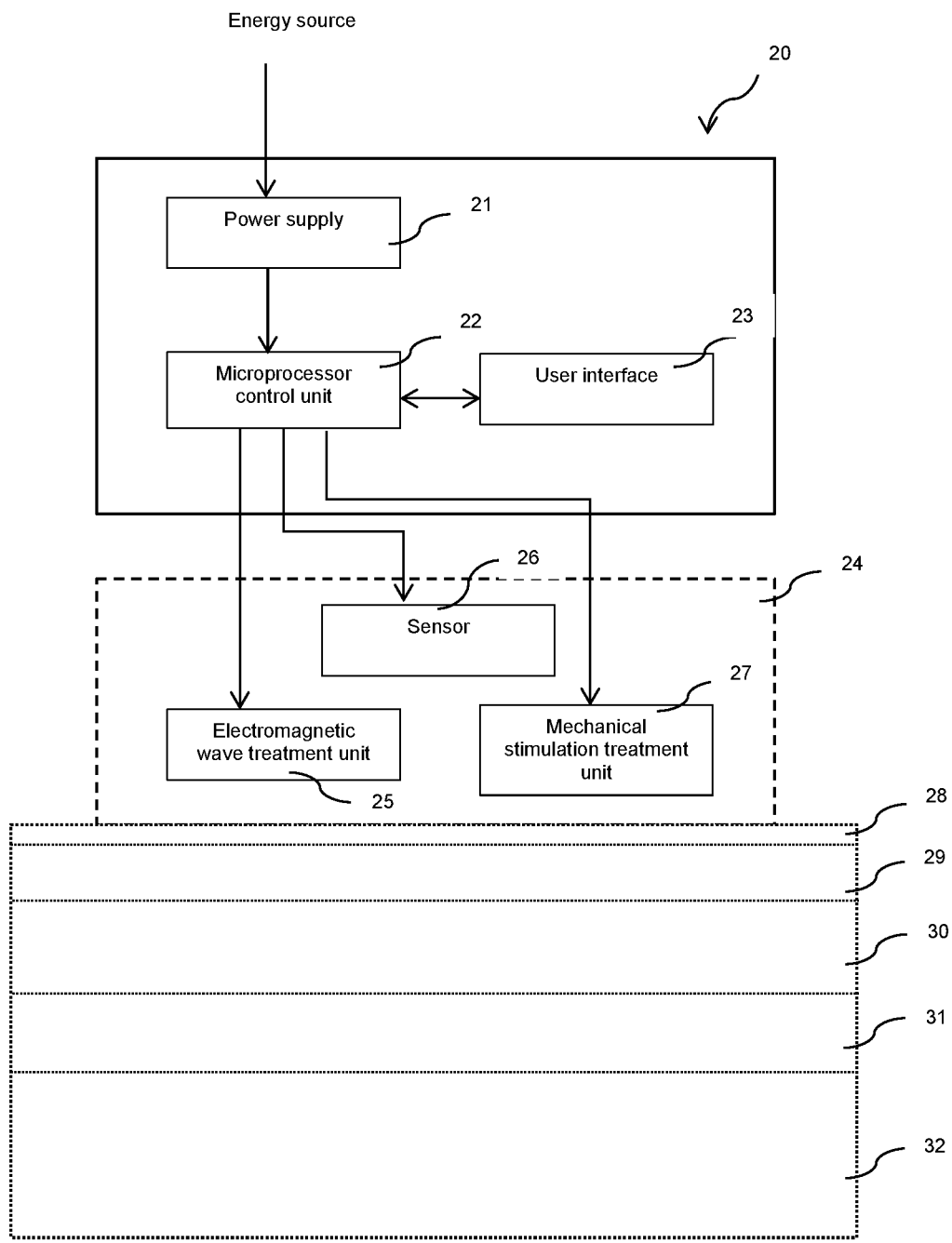
FIG. 2 is a schematic example of positioning of the system for skin treatment

FIG. 2 shows schematic example of positioning of the system for skin treatment. The system for skin treatment 20 applies a combination of electromagnetic and mechanical stimulation energy into the soft tissue. The system may include a power supply 21 connected to an energy source. The system for skin treatment 20 includes at least one applicator 24 which may be placed inside a case or may be separated from the system for skin treatment 20 and connected by a cable. The microprocessor control unit 22 with user interface 23 provides communication between the electromagnetic field treatment unit 25 and mechanical stimulation treatment unit 27. User interface 23 allows setting up the treatment parameters and also may provide the operator various treatment information. User interface 23 may include display. The electromagnetic field treatment unit 25 and mechanical stimulation treatment unit 27 may be placed in at least one applicator 24. However, the treatment units may also have separate applicators. The applicator 24 may preferably contain a sensor unit 26

The output power of the power supply 21 may be in the range of 10 W to 600 W, preferably in the range of 50 W to 500 W, most preferably in the range of 80 W to 450 W.

The sensor unit 26 may contain one or more sensors for sensing temperature, resistance, movement, contact with skin or force applied to skin. The sensor may be invasive or contactless. The sensor may measure one or more physical quantities of the treated tissue and/or untreated tissue.

The temperature sensor measures and monitors the temperature of the treated tissue. Temperature can be analyzed by a microprocessor control unit 22. The temperature sensor may be a contact sensor, contactless sensor (e.g. infrared temperature sensor) or invasive sensor (e.g. a thermocouple) for precise temperature measuring of deep layers of soft tissue. The microprocessor control unit 22 may also use algorithms to calculate the deep or upper-most. A temperatures feedback system may control the temperature and based on set/pre-set limits, alert the operator in human perceptible form e.g. on the user interface 23. In a limit temperature condition, the device may be configured to adjust output power, activate cooling or stop the therapy. Human perceptible form may be sound and/or change of color of the applicator 24 and/or the tip.

A resistance sensor may measure the skin resistance, since it may vary for different patients, as well as the humidity, wetness and sweat may influence the resistance and therefore the behavior of the skin to electromagnetic field. Based on the measured skin resistance, the skin impedance may also be calculated.

The contact and/or force applied by the applicator on the skin surface may be measured piezoresistively, mechanically, optically, electrically, electromagnetically, magnetically or by other attitudes. The measured information from the contact and/or force sensor may influence the start of the therapy or generation of electromagnetic or mechanic field by treatment units. Information about the contact and/or force applied on the skin surface may be presented in human perceptible form to the operator.

Information from one or more sensors may be used for generation of a pathway on a convenient model e.g. a model of the human body shown on the display. The pathway may illustrate a surface and/or volume of already treated tissue, presently treated tissue, tissue to be treated, and/or untreated tissue. A convenient model may show a temperature map of the treated tissue providing information about the already treated tissue or untreated tissue.

The sensor may provide information about the location of bones, inflamed tissue and/or joints. Such types of tissue may not be targeted by mechanical stimulation due to the possibility of painful treatment. Bones, joints and/or inflamed tissue may be detected by any type of sensor such as an imaging sensor (ultrasound, IR sensor), impedance sensor and the like. A detected presence of these tissue types may cause generation of human perceptible signal, interruption of generation of electromagnetic energy and/or mechanical stimulation energy. Bones may be detected by a change of impedance of the tissue and/or by analysis of reflected mechanical waves and/or electromagnetic waves.

The system for skin treatment 20 generates electromagnetic waves and mechanical stimulation enabling improvement of the soft tissue, mainly connective tissue in the skin area. The connective tissue in the skin area contains layer epidermis 28 and dermis 29; white adipose tissue in hypodermis 30 and peritoneal cavity 32. The other soft tissue below the skin area e.g. muscular tissue 31 remains untreated and unharmed. The therapy may stimulate the blood circulation or may also create micro-disruptions of treated tissue, and/or create movement, rotation or polarization of particles by induced current and/or magnetic field which increase the temperature of treated tissue. The combined therapy may result in increased cell membrane permeability, which may result in increased liquefying of fat and/or lipolysis. Combination of both therapies highly reduces the risk of adipocytes inflammation.

Without being bound to the theory, it is believed that the mechanical stimulation may increase the penetration depth and enable remodeling of the visceral white adipose tissue which is located in the peritoneal cavity 32. The mechanical stimulation, in combination with electromagnetic field, may result in reduction of visceral fat cells. Therefore the overall number and/or volume of SWAT and/or VWAT may be reduced. Temperature of the treated tissue during the therapy may be increased to about 32-48° C.

Also neovascularization may be induced based on increased angiogenic grow factors VEGF, and also PCNA, NOS etc. Improvement of microvascular network may also result in better lipid metabolism functionality.

Another soft tissue improvement is in the field of tissue elasticity. The micro-disruptions also lead to improved tissue regeneration and in combination with electromagnetic field therapy induces neocollagenesis, neoelastogenesis and improvement of tissue elasticity. Although neocollagenesis is normally induced at higher temperatures than 32-48° C., the combination of mechanical stimulation and electromagnetic field enables improved results at temperatures in this range, resulting in less stress of the tissue. The treatment may include at least partial destruction and subsequent repair and/or synthesis of other forms of connective tissue, e.g. fibronectin, matricellular protein etc.

Transfer of the energy may change attributes of the tissue. Temperature of the tissue may be increased to about 32-48° C.

Method and device may include direct contact of the applicator 24 with the tissue which may result in a deflection of the tissue by the application of mechanical stimulation. The deflection may be in the range of 0.01 mm to 30 mm or 0.01 mm to 20 mm or 0.05 to 10 mm.

Because of the direct contact of the applicator 24 with the tissue, a recess in the tissue may be formed during treatment. The recess may be in the range of 0.001 cm to 8 cm or 0.01 cm to 6 cm or 0.05 to 4 cm or 0.01 cm to 3.5 cm.

The electromagnetic field and mechanical stimulation may be applied with a frequency ratio which provides significant results, convenient treatment and minimal adverse effects. The ratio between the electromagnetic field frequency and mechanical stimulation frequency (MHz/Hz) may be in the range of 0.005 to 60 or 0.01 to 28.

The mechanical stimulation also have an analgesic and myorelaxative effects which increase the comfort of therapy.

Treatment may be performed on the whole surface of the body or it may include particular parts of body e.g. face, neck, breasts, shoulders, thorax, abdomen, waistline, genitals, region of love handles, sides of the torso (e.g. bra fat), arms, buttocks, saddlebag, thighs, and calf. Treatment of face may include treatment of wrinkles, cheek lifting and/or treatment of crooked nose. Treatment of neck may include treatment of swelling tissue. Treatment of arms may include treatment palms, nails, cuticles, nail beds. Treatment of arms may include treatment of bingo wings. Treatment of genitals may include treatment of penis and/or scrotum. Treatment of the breasts may include treatment of the Cooper ligament and/or breast lifting. Treatment of buttocks may include butt lifting. Treatment of the body may include treatment of tissue above and/or adjacent to at least one lymph node, wherein treatment of the lymph node may provide lymph flow stimulation, treatment of lymphedema and/or lymph filtering stimulation. The present method and device may be used for treatment of sexual problems e.g. erectile dysfunction. Treatment may be targeted to the cavities of the body e.g. mouth, vagina and anus.

In another embodiment, the device may include a suction unit. The suction unit provides a vacuum or negative pressure on the treated skin. The suction unit may improve the contact mechanical stimulation treatment unit and/or electromagnetic field treatment unit with the skin surface and ensure better therapy.

The arrangement of mechanical stimulation treatment unit 27 and electromagnetic wave treatment unit 25 may be in one or more separate applicators 24. Where one applicator is used, the applicator 24 may contain one treatment energy delivery element designed for transmission of mechanical stimulation and electromagnetic waves into the soft tissue. However, the mechanical stimulation treatment unit 27 and electromagnetic wave treatment unit 25 may be designed with separate energy delivery elements organized in concentric, axial symmetrical or non-symmetrical ways.

Applicator 24 includes surface contacting the tissue including one or more energy delivery elements transmitting electromagnetic waves and one or more energy delivery element designed to transmit mechanical stimulation. The surface of a first energy delivery element is designed to transmit electromagnetic waves and a surface of a second energy delivery element is designed to transmit mechanical stimulation. The effective surface areas of the first and second energy delivery elements may have different ratios. The surface of first energy delivery element designed to transmit electromagnetic waves may cover at least 20%, more preferably 30%, still more preferably 35% and more preferably 40% of the applicator's surface contacting the tissue. The surface of second energy delivery element designed to transmit mechanical stimulation may be described as percussion guide.

The surface of the second energy delivery element may be at least 0.03 cm$^2$, or in the range of 0.05 cm$^2$ to 50 cm$^2$, more preferably in the range of 0.75 cm$^2$ to 40 cm$^2$, most preferably in the range of 0.1 cm$^2$ to 35 cm$^2$.

Surfaces of energy delivery elements providing electromagnetic field and mechanical stimulation may be in the different ratio, which was found to deliver most of the energy used for treatment. The ratio of the surface of the first energy delivery element providing the electromagnetic field to the surface of the second energy delivery element providing mechanical stimulation may be in the range of 0.01 to 80 or 0.05 to 65 or 0.1 to 50 (with the surface areas referring to the surface area of each element intended to make contact with the skin).

Movement of one or more applicators 24 may be provided by a robotic system, which may be controlled by the operator using the user interface 23. The robotic system may be also operated in automated manner, which may be guided in a pathway provided by a sensor.

Figure 6:
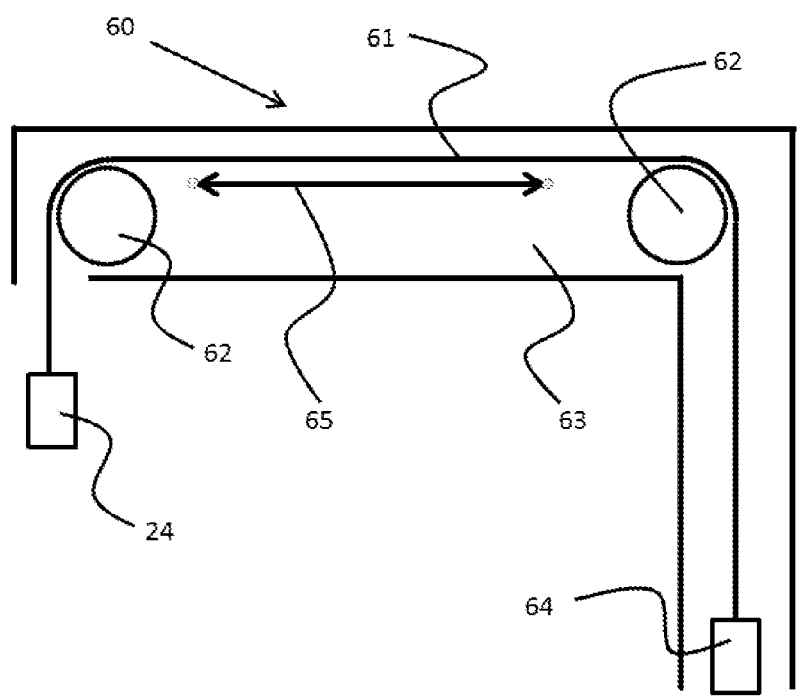
FIG. 6 is a schematic diagram of a device for an assisting movement element which may increase and/or decrease the pressure applied on the tissue by an applicator.

FIG. 6 shows a device including an assisting movement element 60 which may increase and/or decrease the pressure applied on the tissue by the applicator 24 and/or device. Assisting movement element 60 may be used with manual movement of the applicator 24 to provide comfortable operation. Assisting movement element 60 may include one or more flexible link 61, sheaves 62 and/or movement elements 64 providing easier control to the applicator 24. Flexible link 61 and sheave 62 are shown to be located in the guiding element 63. Rope 61 may be moved in directions of the arrow 65. Forward movement of the flexible link 61 may increase the pressure applied by the applicator 24 on the tissue. Backward movement of the flexible link 61 may be enhanced by movement element 64 providing decreased weight of the applicator. Both these types of movement may be enhanced by movement element 64. Treatment may include combination of both movements in order to provide sufficient pressure and/or reduced fatigue of the operator by decreased weight of the applicator.

The methods and device described may provide an overall solution for soft tissue treatment, mainly in skin region including reduction in size and or volume of fat cells. The therapy also enables improvement of cellulite. The cellulite may be treated preferably without shrinkage of collagen fibers, since the triple helix structure is not denatured. Instead the method and system cause only micro-disruption at increased temperatures in the range 32-48° C. which increases the repair processes and collagen deposition.

The method and device combining shockwave energy and other types of energy (e.g. radiofrequency, light, microwave) also provide treatment of dermatitis, atrophic disorders (e.g. stretch marks), wrinkles, dimpled skin, mycosis, warts, herpes simplex, bacterial cellulitis, post surgical fibrosis, dry eye syndrome, periorbital skin laxity, melbomian fland dysfunction, hair growth stimulation, and/or hypertrophic disorders (e.g. scar). While analgesic effects of mechanical stimulation may provide dermatitis patient with relief of pain or itching, radiofrequency may provide heat causing at least partial regeneration of the tissue, initiation of the immunological response and/or its enhancement. Stretch marks may be treated by causing micro-disruption of the connective tissue and subsequent synthesis of new connective tissue. The method and device may also provide circumferential reduction, pain relief, body contouring, enhancement of lymphatic drainage, wound healing, enhancement of hyperaemia, improvement of microcirculation, improvement of vascularization, improvement of blood flow, improvement of tissue oxygenation, improvement of body fluids flow, skin tightening, rejuvenation of skin, tightening of lax skin (e.g. after liposuction), improvement of skin elasticity, enhancement of skin hydration, myorelaxation, muscle regeneration, muscle volumization, removal of varices, removal of calcium deposits, removal of apthoous stomatitis, removal of birthmarks, removal of ganglion cyst, and/or removal or correction of pigment deficiencies (e.g. rosacea, pigment stains, cafe au lait spots, port-wine stains). The method and device may also provide treatment of Achilles tendonitis, ankle distortion, anterior tibial syndrome, arthritis of the hand, arthrosis, bursitits, carpal tunnel syndrome, cervical pain, dorsalgia, epicondylitis, facial nerve paralysis, herpes labialis, hip joint arthrosis, impingement syndrome/frozen shoulder, knee arthrosis, knee distortion, lumbosacral pain, muscle relaxation, nerve repair, onychomycosis, Osgood-Schlatter syndrome, pain relief, painful shoulders, patellar tendinopathy, plantar fasciitis/heel spur, tarsal tunnel syndrome, tendinopagny and/or tendovaginitis. The method and device may be used for enhancement of membrane transport of active substance (e.g. drug). The method and device may be used for improvement bone healing, wound healing and/or post surgical regeneration of the wound.

The method and device may be used for treatment of animals, e.g. dog, cat, guinea-pig, horse, cattle, sheep, goat, zebu, chicken, donkey, duck, buffalo, camel, goose, yak, llama, alpaca, rabbit, fox, deer, bear, reindeer, oryx, gazelle, giraffe, hyena, cheetah, elk, bison, muskox and/or lynx. In such case, the method and device may provide treatment of lumbosacral disease, elbow dysplasia, hip dysplasia, intervertebral disc disease, lick granuloma, carpus osteoarthritis, elbow osteoarthritis, hip osteoarthritis, stifle osteoarthritis, tarsus osteoarthritis, inflammation sesamoids, shoulder instability, carpus tendonitis, elbow tendonitis, hip tendonitis, stifle tendonitis, tarsus tendonitis, navicular disease (podotrochleosis), back pain, chronic tendonitis, pseudoarthrosis, exostosis, osteitis, bursitis, ringbone, post surgical pain, splints, neck pain, myofascial pain, neuropathy, navicular syndrome, hunter's bumps, hip dysplasia, degenerative joint disease, cauda equine syndrome, epiphysitis, capped hock, bone spavin, bucked shins, abscesses, anal sacculitis, aural hematoma, burns, bites, feline acne, fractures, gingivitis, snake bite, mucoskeletal pain, otitis, peri-anal fistula, periodontal disease, pyotraumatic dermatitis, rhinitis, sinusitis, stomatitis, muscle trigger points and/or acute moist dermatitis. The method and device may be used for improvement bone healing, wound healing and/or post surgical regeneration of the wound.

Figure 3A:
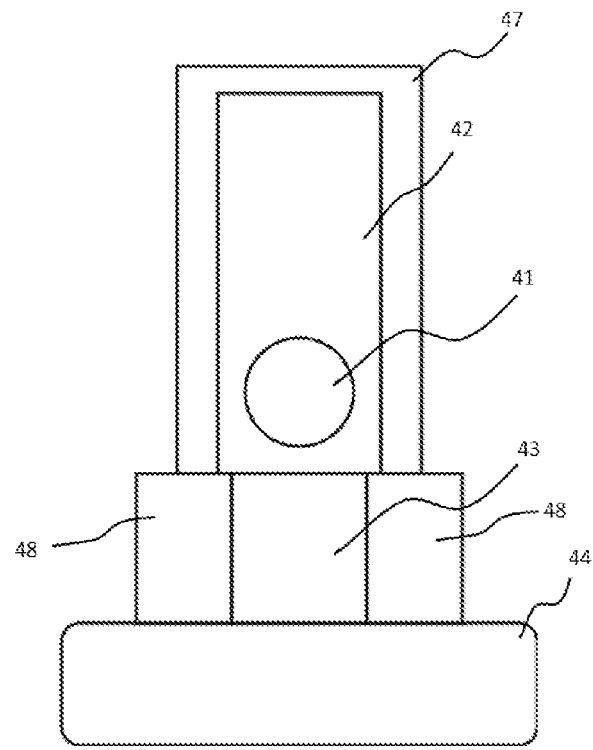
FIG. 3A is a schematic exemplary cross section of an applicator.
Figure 3B:
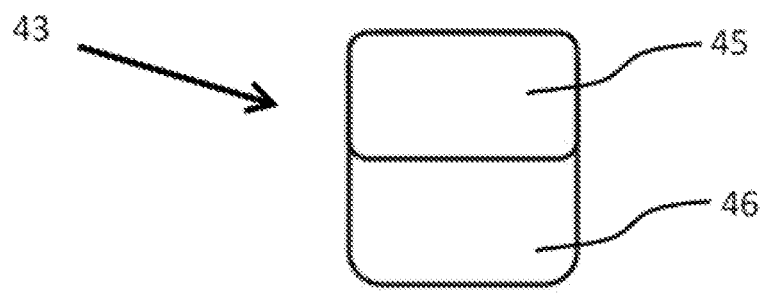
FIG. 3B is a schematic example of a percussion guide.

FIG. 3A shows exemplary cross section of applicator operated on ballistic principle including a bullet 41 inside a guiding tube 42 (enclosed in casing 47) striking to the percussion guide 43 representing an energy delivery element designed to transmit mechanical stimulation. Electrode 48 represents an energy delivery element designed to transmit electromagnetic waves. Generated mechanical stimulation is transmitted to the tissue 44. Percussion guide 43 may be constructed as one piece and it may include impact part 45 and tissue-facing part 46 (shown of FIG. 3B). In another embodiment percussion guide 43 may be divided into impact part 45 and tissue-facing part 46, wherein both parts have different characteristics. Impact part 45 may be embedded into tissue-facing part 46 and vice versa. Impact part 45 may be part of the guiding tube 42. More than one percussion guide 43 may be used.

The applicator and/or energy delivery elements (e.g. electrode 48 and/or percussion guide 43) may be detachable. Detaching these elements may ease cleaning the coupling medium (e.g. gel), used to transfer of the electromagnetic field and mechanical stimulation, from the system. Excess coupling medium may build up in a space between the percussion element 43 and electrode by movement of the applicator. Therefore, detaching these parts may provide a more reliable way of cleaning the system. The electrode 48 and/or percussion guide 43 may be detachable from the rest of the applicator. Optionally only electrode 48 or percussion element 43 may be detachable from the applicator 24.

Alternatively, the electrode 48 and percussion element 43 may be provided as one part of the device. In this case, the resulting element has characteristics of a percussion element and an electrode, therefore heating may be provided by the same surface delivering mechanical stimulation. Such configuration may prevent the disposition of the coupling medium on the applicator.

The system may also recognize the attached percussion element 43 and/or electrode 48 and allow only predefined treatments and/or set safety limits of the treatment related to the attached percussion element 43 and/or electrode 48.

The applicator may include a reservoir of medium (e.g. fluid and/or gel) for transferring mechanical stimulation. The reservoir may be located between tissue-facing part 46 of the percussion guide 43 and the wall contacting the tissue. Optionally, the applicator may include an assembly of two or more percussion guides transferring mechanical stimulation to the tissue through the reservoir. The reservoir may be detachable.

Percussion guide 43, impact part 45 and/or tissue-facing part 46 may be made from variety of materials e.g. metal, polymer, ceramic, glass, and/or natural material (e.g. bone, wood etc.). Furthermore, impact part 45 and/or tissue-facing part 46 may be made from different materials. Metals used may be titanium, chromium, manganese, aluminum, cobalt, vanadium and/or alloys. Such alloy may be e.g. stainless steel, Inconel, Nimonic and the like. Polymer may be thermoplastic polymer (e.g. polyurethane), polyepoxides, acrylate polymers, fibre-reinforced polymer (e.g. polyoxymethylene, carbon fiber reinforced polymer), and/or fluoropolymer. In another exemplary embodiment polymer may be Kevlar, rubber or silicone. Ceramic may be sintered ceramic.

Percussion guide 43 and/or its parts may be made of biocompatible composite coated with nanoparticles e.g. nano-carbon particles. Composite material may be e.g., ceramic, hydroxyapatite, fullerenes, carbon fiber reinforced polymer etc.

Percussion guide 43, impact part 45 and/or tissue-facing part 46 may be coated and/or covered by a layer of any of the materials mentioned above, and/or by any polymer (e.g. fluorocarbons), metal and/or vitreous enamel. A covering layer may be detachable from the percussion guide 43 and/or its parts.

One or more sensors may provide information about the temperature, shape and/or position of the percussion guide 43. The position of the percussion guide 43 may be changed by the striking of the bullet 41. When the bullet 41 changes the secured position of the percussion guide 43 in the guiding tube 42, the system may alert the operator in human perceptible form e.g. on the user interface 23. The system may also receive information about the state of the percussion guide 43, e.g. the number of strikes by the bullet 41. Based on such information, system may calculate the estimated number of future strikes of the bullet 41 and inform the operator about estimated lifetime of the percussion guide 43. The system may inform the operator by any human perceptible form.

Percussion guide 43, impact part 45 and/or tissue-facing part 46 may have any shape. Percussion guide 43 may have ellipsoidal or cylindrical shape with one or more recess. The impact part 45 may have a greater dimension than the tissue-facing part 46 causing increased pressure on the tissue providing a more focused effect. Optionally, the impact part 45 may have smaller dimensions than the tissue-facing part 46 providing decreased pressure and a more distributed effect. The tissue-facing part 46 may have a concave, convex and/or flat surface contacting the tissue. Concave surfaces and variations of the dimension of such shape may provide control of focus and/or penetration depth of the mechanical stimulation. Flat and/or convex surfaces may provide defocused and/or radial mechanical stimulation.

Percussion guide 43 and/or at least one of its parts may be cooled and/or heated, as controlled by the microprocessor control unit 22. Heating and/or cooling of the percussion guide 43 may influence the characteristics of transmitted mechanical stimulation and/or the temperature of the electrode 48 transmitting electromagnetic energy.

Figure 3C:
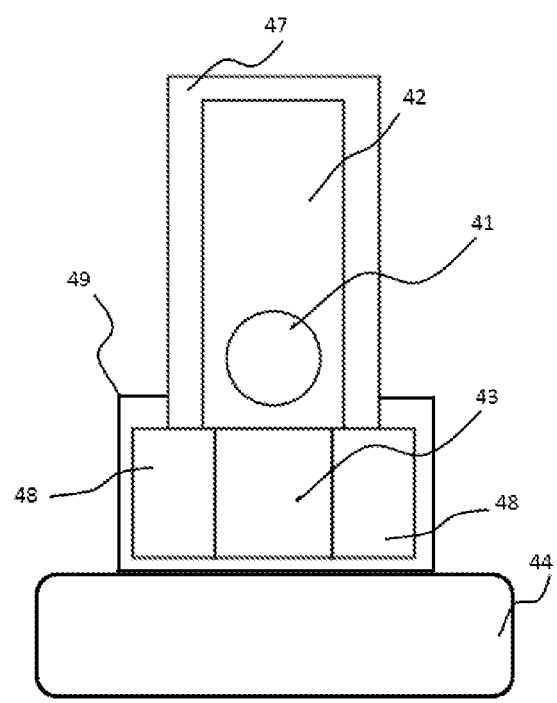
FIG. 3C is a schematic cross section of another applicator.

Applicator 24 may be covered by a protective sheath 49 shown on FIG. 3C during the treatment. The protective sheath 49 may be made of polymer and/or natural fibers. The protective sheath may separate applicator 24 from the tissue, protecting the applicator from disposition of an excess of the coupling medium. In another embodiment the protective sheath may separate apparatus from the coupling medium applied on the tissue. The protective sheath may be disposed after the treatment.

Treatment of soft tissue may be provided without using the coupling medium. Applicator 24 may include percussion guide 43 or tissue-facing part 46 having a smooth surface, which is made of and/or coated with polymer e.g. polytetrafluoroethylene. The treated tissue may be covered by material providing smooth surface for the movement of the applicator 24.

The bullet 41 in the guiding tube 42 may be accelerated by the pressurized gas. Gas may be pressurized by pressure in the range of 0.1 bar to 50 bar, more preferably in the range of 0.2 bar to 45 bar, most preferably in the range of 0.5 to 35 bar.

Soundproofing elements may be used for reducing the noise generated by the operation of the system. One soundproofing element may be an isolation tube positioned around the guiding tube 42 and/or the percussion element 43. Hence, the isolation tube may form isolation space around the mechanical stimulation treatment unit 27 and be a part of applicator 24. Isolation space may separate guiding tube 42 and/or percussion element 43 from the rest of the device by a layer of isolation material e.g. air, gas, solid substance and/or gel. Solid substances possessing soundproofing characteristics and elasticity may be e.g. silicone, melamine foam, melamine and/or resin. In still another embodiment the device may include one or more sensors providing information which may be used for analysis of the noise. The isolation space may include one or more elements providing destructive interference to the noise. According to one illustrative embodiment, protective sheath 49 may also have function of the soundproofing element.

Briefly stated, a method for soft tissue treatment of a patient includes positioning an applicator adjacent to the soft tissue of the patient; transmitting mechanical stimulation into the soft tissue of the patient causing mechanical stimulation of the soft tissue of the patient; transmitting electromagnetic waves from the applicator into the soft tissue with the electromagnetic waves heating the soft tissue; and remodeling soft tissues via the combination of mechanical stimulation and electromagnetic waves. The method may remodel the soft tissue and cause reduction of the VWAT and/or the SWAT; reduction in the number of adipose cells; reduction in the volume of adipose cells; and/or improve connective tissue elasticity or cellulite appearance. The method may also improve elasticity of fibrous septae connecting the dermis to underlying fascia.

Methods of treatment may include stimulation of flow of the lymph through the lymphatic system providing faster transfer of remnants of lipolysis. The weight of the applicator, reinforced by assisting movements, together with proper movement of the applicator may increase the velocity of flow of the lymph through the lymph vessels. Proper movement of the applicator may be performed by the operator through direct or indirect control and/or by a robotic system. The applicator may be moved in continuous longitudinal movements, which may have any shape e.g. loop, circular and/or random. The applicator may be also moved in straight line. Movement of the applicator may be in the direction from the center of the treated part of the body to its periphery. Movement of the applicator may also be in the direction from the periphery of the treated part of the body towards the center of the body. Continuous movement may be directed to one or more lymph nodes e.g. lymph nodes in the groins. Treatment may enhance blood flow in the adipose tissue, which may lead to increased heat distribution to adjacent volumes of treated and/or untreated tissue.

Figure 4:
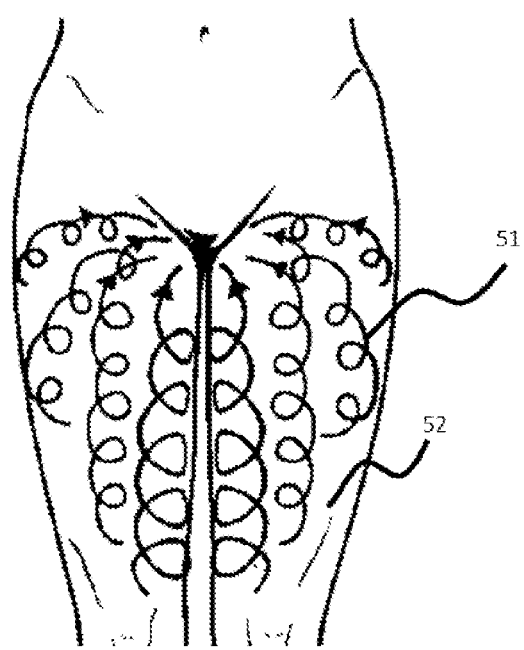
FIG. 4 is a schematic example of movement of the applicator.

The treatment may include straight or continuous circular movement of the applicator towards the lymph nodes in the groins. FIG. 4 shows an example of treatment of front thigh 52. The direction of movements 51 toward the groins may cause stimulation of lymph flow to the lymph node. The treatment of the abdomen may include movement of the applicator toward one or more lymph nodes located in the abdomen. The treatment of the arm may include straight or continuous circular movement of the applicator towards the lymph node located in the underarms. The treatment of the head may include straight or continuous circular movement of the applicator towards the one or more lymph nodes located in the head or neck e.g. a circular lymph node, parotid node, submental node, submandibular node and/or occipital node.

Thus, novel apparatus and methods have been shown and described. Various changes and substitutions may of course be made without departing from the spirit and scope of the invention. The invention, therefore, should not be limited except by the following claims and their equivalents.

The invention claimed is:

1. A device for treating a patient by a combination of radiofrequency and mechanical energy, the device comprising:
  a case comprising:
    a power supply;
    an energy source configured to generate a radiofrequency energy with a frequency in a range of 0.1 MHz to 435 MHz;
    a control unit configured to control the energy source; and
    a user interface comprising a display and configured to allow a user of the device to set up treatment parameters; and
  an applicator connected with the case by a cable and configured to provide a combination of a mechanical stimulation and the radiofrequency energy to a skin of the patient, the applicator comprising:
    a mechanical stimulation treatment unit comprising a mechanical energy delivery element configured to apply a gas having a positive pressure in a range of 0.5 bar to 35 bar to the skin configured to provide a massage of the skin;
    wherein the mechanical energy delivery element has a surface area in a range of 0.1 cm$^2$ to 35 cm$^2$; and
    wherein a repetition rate of the mechanical stimulation is in a range of 0.1 Hz to 100 Hz;
    a first radiofrequency electrode configured to provide the radiofrequency energy to the skin in order to heat the skin of the patient;
    a second radiofrequency electrode configured to provide the radiofrequency energy to the skin in order to heat the skin of the patient;
    wherein the first radiofrequency electrode and the second radiofrequency electrode create a bipolar electrode system;
    wherein the bipolar electrode system is not in contact with the skin; and
    a plurality of temperature sensors configured to measure a temperature of the treated skin;
    wherein the control unit is configured to analyze the measured temperature and configured to control the mechanical stimulation and the radiofrequency energy according to the set up treatment parameters.

2. The device of claim 1, wherein the radiofrequency energy is in a range of 0.1 MHz to 28 MHz.

3. The device of claim 1, wherein a ratio of surface areas of the first radiofrequency electrode and the mechanical energy delivery element is in a range of 0.01 to 80.

4. The device of claim 1, wherein the bipolar electrode system is configured to cause heating of the skin to a temperature in a range of 32° C. to 48° C.

5. The device of claim 1, wherein the applicator is configured to be in direct contact with the skin.

6. The device of claim 5, wherein the mechanical stimulation is configured to provide a deflection of the skin in a range of 0.05 mm to 10 mm.

7. The device of claim 1, wherein the first radiofrequency electrode is an inductive electrode and wherein the mechanical energy delivering element comprises a guiding tube or a percussion guide.

8. A device for treating a patient, the device comprising:
an energy source configured to generate a radiofrequency energy with a frequency in a range of 0.1 MHz to 25 GHz;
a control unit comprising a microprocessor configured to control the energy source;
a user interface comprising a display and configured to allow a user of the device to set up treatment parameters; and
an applicator configured to be in contact with a tissue of the patient and to provide a mechanical stimulation and the radiofrequency energy to the tissue, the applicator comprising:
a mechanical energy delivery element having a surface area in a range of 0.05 cm$^2$ to 50 cm$^2$ and configured to apply a gas to the tissue configured to provide a massage of the tissue;
wherein the gas has a positive pressure in a range of 0.1 bar to 50 bar; and
wherein a repetition rate of the mechanical stimulation is in a range of 0.5 Hz to 50 Hz;
a pair of bipolar radiofrequency electrodes in a non-contact arrangement with a skin of the patient and configured to provide the radiofrequency energy to the tissue in order to heat the tissue of the patient to a temperature in a range of 37° C. to 200° C.; and
one or more temperature sensors configured to measure the temperature of the treated tissue and provide the measured temperature to the control unit;
wherein the control unit is configured to control the mechanical stimulation and the radiofrequency energy according to the set up treatment parameters; and
wherein the control unit is configured to analyze the measured temperature and alert the user of the device when the temperature reaches a pre-set limit.

9. The device of claim 8, wherein the pair of bipolar radiofrequency electrodes is configured such that a distance between the electrodes is variable.

10. The device of claim 8, wherein an energy flux density of the radiofrequency energy is in a range between 0.01 mW·mm$^{-2}$ and 10 000 mW·mm$^{-2}$.

11. The device of claim 8, wherein a sum of an energy flux density of the mechanical stimulation and the radiofrequency energy applied to the patient is in a range of 0.1 mW·mm$^{-2}$ to 15000 mW·mm$^{-2}$.

12. The device of claim 8, wherein the control unit is configured to provide the radiofrequency energy and the mechanical stimulation simultaneously for at least a subset of a duration of the treatment.

13. The device of claim 8, wherein the radiofrequency energy has a frequency in a range of 0.1 MHz to 28 MHz.

14. The device of claim 8, wherein the radiofrequency electrode is detachable from the applicator.

15. A method for treating tissue of a patient, the method comprising:
generating a radiofrequency energy with a frequency in a range of 0.1 MHz to 25 GHz via an energy source;
positioning an applicator adjacent to a tissue of the patient;
setting up treatment parameters with a user interface comprising a display;
connecting an applicator with the energy source via a cable;
wherein the applicator comprises a mechanical energy delivery element configured to provide a mechanical stimulation, a radiofrequency electrode configured to provide the radiofrequency energy, and a temperature sensor;
providing a massaging effect to the patient via the mechanical stimulation from the mechanical energy delivery element into the tissue of the patient with the mechanical stimulation at a frequency in the range of 0.1 Hz to 100 Hz;
wherein the mechanical stimulation is caused by a pressurized gas having a positive pressure in a range of 0.5 bar to 30 bar;
transmitting the radiofrequency energy from the radiofrequency electrode into the tissue of the patient with the radiofrequency energy configured to heat the tissue of the patient;
wherein the radiofrequency electrode is not in contact with the tissue of the patient during the treatment;
measuring a temperature of the treated skin during the treatment with the plurality of temperature sensors; and
remodeling the tissue of the patient via the combination of the mechanical stimulation and the electromagnetic energy.

16. The method of claim 15, further comprising maintaining the temperature of the tissue of the patient in a range of 32° C. to 48° C.

17. The method of claim 15, further comprising:
transmitting the measured temperature measured by the plurality of temperature sensors to the control unit;
evaluating the measured temperature with the control unit; and
alerting the user of the device when the measured temperature reaches pre-set limit; or
adjusting an output power of the radiofrequency or stopping the therapy when the measured temperature reaches a limit temperature condition.

18. The method of claim 15, further comprising:
positioning the applicator in direct contact with the tissue of the patient; and
providing a deflection of a skin of the patient in a range of 0.05 mm to 10 mm via the mechanical stimulation.

19. The method of claim 15, wherein the radiofrequency energy has a frequency in a range of 0.1 MHz to 28 MHz.

20. The method of claim 19, further comprising transmitting the radiofrequency energy from the second radiofrequency electrode into the tissue of the patient to heat the tissue of the patient;
wherein the radiofrequency electrode and the second radiofrequency electrode form a pair of bipolar radiofrequency electrodes; and wherein the pair of bipolar radiofrequency electrodes is positioned in the applicator such that the electrodes are not in contact with the patient.

\* \* \* \* \*

UNITED STATES PATENT AND TRADEMARK OFFICE
CERTIFICATE OF CORRECTION

| | | |
|---|---|---|
| PATENT NO. | : 12,220,380 B2 | Page 1 of 1 |
| APPLICATION NO. | : 18/051748 | |
| DATED | : February 11, 2025 | |
| INVENTOR(S) | : Tomáš Schwarz | |

It is certified that error appears in the above-identified patent and that said Letters Patent is hereby corrected as shown below:

On the Title Page

Item (72) Please correct the spelling of the name of the Inventor to:
Tomáš Schwarz Signed and Sealed this
Eighth Day of April, 2025

Coke Morgan Stewart
*Acting Director of the United States Patent and Trademark Office*